(12) United States Patent  (10) Patent No.: US 8,474,321 B2
Seltzer  (45) Date of Patent: Jul. 2, 2013

(54) LIGHTED GAUGE

(76) Inventor: Michael Seltzer, Valley Stream, NY (US)

( * ) Notice: Subject to any disclaimer, the term of this patent is extended or adjusted under 35 U.S.C. 154(b) by 503 days.

(21) Appl. No.: 12/780,332

(22) Filed: May 14, 2010

(65) Prior Publication Data

US 2011/0282218 A1  Nov. 17, 2011

(51) Int. Cl.
*G01L 7/00* (2006.01)
(52) U.S. Cl.
USPC ............................................................ 73/700
(58) Field of Classification Search
USPC .................................................. 73/700–756
See application file for complete search history.

(56) References Cited

U.S. PATENT DOCUMENTS

| | | | |
|---|---|---|---|
| 2,761,056 A | 8/1956 | Lazo | |
| 3,699,915 A | 10/1972 | Greene | |
| 4,275,393 A * | 6/1981 | Johnston | 340/688 |
| 4,300,548 A * | 11/1981 | Jones | 128/204.21 |
| 4,970,400 A | 11/1990 | Muramatsu | |
| 5,050,527 A | 9/1991 | Kameda | |
| 5,920,150 A | 7/1999 | Crary et al. | |
| 6,019,730 A | 2/2000 | Rashman et al. | |
| 6,206,533 B1 | 3/2001 | Shi | |
| 7,716,990 B1 * | 5/2010 | Sacerio | 73/700 |
| 2003/0012359 A1 | 1/2003 | Nayhouse et al. | |
| 2008/0002386 A1 | 1/2008 | Mezouari | |
| 2008/0074863 A1 | 3/2008 | Golle | |
| 2009/0044631 A1* | 2/2009 | Neighoff, Jr. | 73/738 |
| 2009/0126482 A1* | 5/2009 | Fundak et al. | 73/293 |

FOREIGN PATENT DOCUMENTS

JP  11-030534  2/1999

* cited by examiner

*Primary Examiner* — Andre Allen
(74) *Attorney, Agent, or Firm* — Sorell, Lenna & Schmidt, LLP

(57) ABSTRACT

An apparatus includes (a) a dial having a front face with indicia thereon and a transparent face plate and a back surface; and (b) a light source attached to the dial and positioned exterior to the transparent face plate and oriented so as to illuminate the face plate. The apparatus is advantageously used to measure blood pressure under adverse lighting conditions.

16 Claims, 5 Drawing Sheets

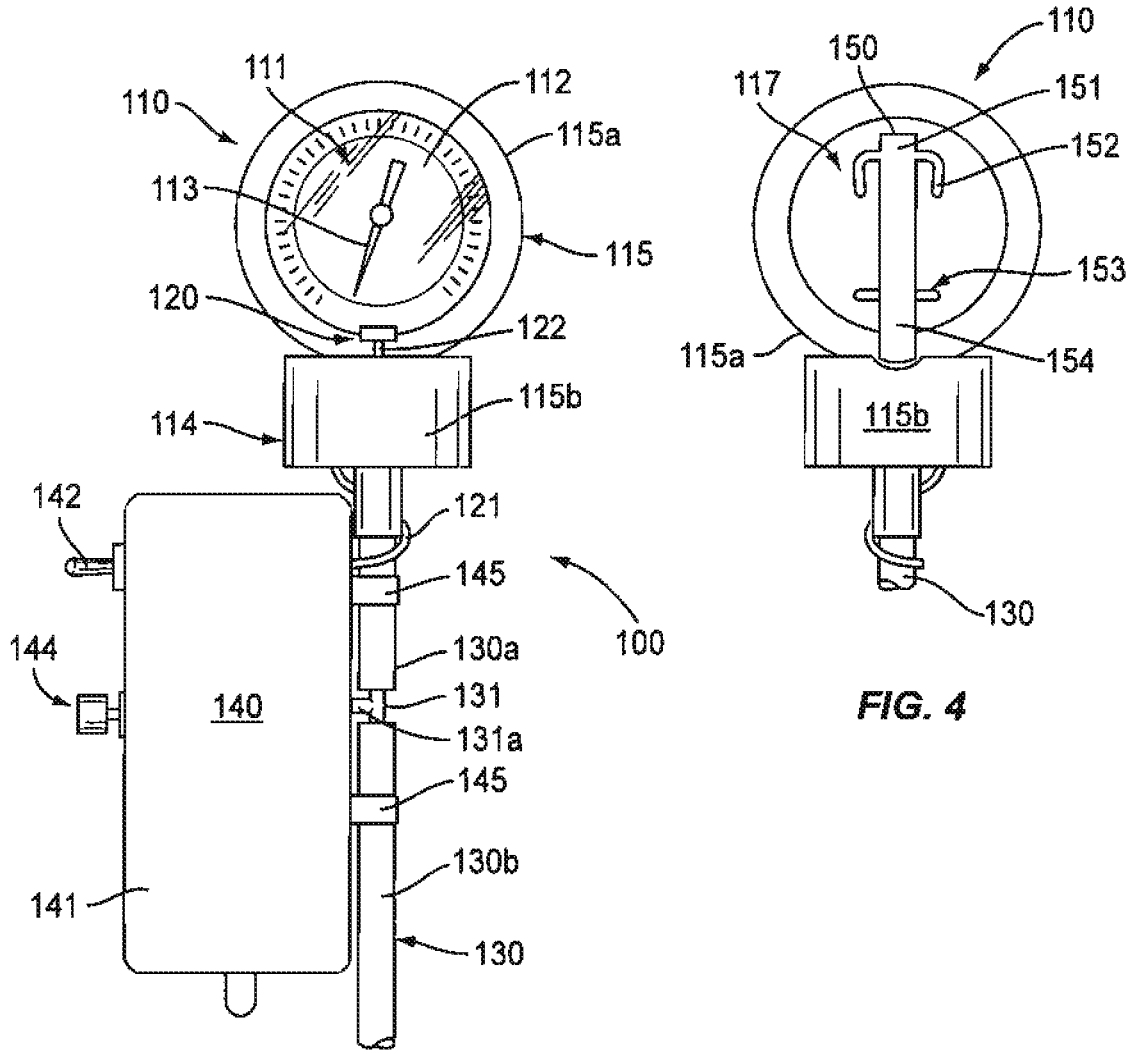
FIG. 3
FIG. 4
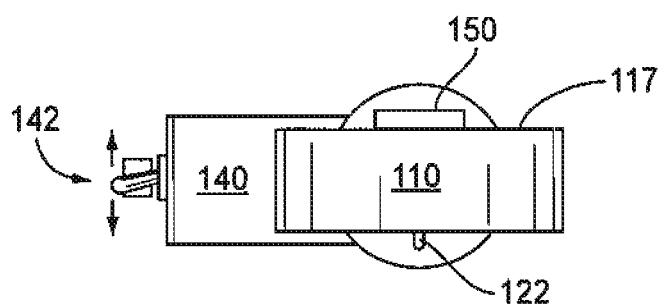
FIG. 5 ued States 8,474,321 B2

LIGHTED GAUGE

BACKGROUND

1. Field of the Invention

The present invention relates to an illuminated gauge, and more particularly to a device for measuring blood pressure having a lighted dial.

2. Background of the Art

Technicians often have to work in all conditions of weather and situations involving poor visibility due to lighting. They have to record the readings in gauges such as pressure gauges. Most gauges currently come with some type of reflective dial. These are somewhat easily seen during daylight hours or when illuminated with an external light source light at night or during diminished light conditions. Medical personnel, especially, may have to measure the blood pressure of patients outside of well lighted medical facilities, for example, during an emergency situation at night. During an emergency, a blood pressure reading can be crucial for detecting internal hemorrhaging. Even absent an emergency, it may be required for a medical technician to measure the blood pressure of a sleeping patient in a darkened hospital room. Turning on the overhead room lights is inconvenient and can disturb and waken the patient.

While various devices and method have been disclosed to provide lighting to the dials of gauges, there is still need for improved lighted gauges, to facilitate reading the dial under low light conditions.

SUMMARY

A lighted gauge apparatus is provided herein. The apparatus comprises (a) a dial having a front face with indicia thereon, a transparent face plate, and a back surface; and (b) a light source attached to the dial and positioned exterior to the transparent face plate and oriented so as to illuminate the front face of the dial.

In an embodiment the invention can include an adapter which can be retrofitted to an existing gauge for providing illumination of the dial face. The retrofittable apparatus includes (a) a cover; (b) a light source associated with said cover; and (c) a regulator electrically connected to the light source, the regulator switching on said light source for a predetermined period of time either (i) automatically in response to actuation of the gauge, or (ii) manually in response to actuation of a regulator first switch associated with said regulator.

The apparatus is advantageously used to measure blood pressure under adverse lighting conditions.

BRIEF DESCRIPTION OF THE DRAWINGS

Various embodiments are described below with reference to the drawings wherein:

FIG. 3 is a front elevational view of the lighted gauge of the invention;

FIG. 4 is a rear view of the meter head of the invention;

FIG. 5 is a top plan view of the lighted gauge of the invention;

DETAILED DESCRIPTION OF PREFERRED EMBODIMENT(S)

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range.

The lighted gauge described herein can be used in conjunction with any apparatus, particularly, measuring apparatus having a dial, which may need to be read under adverse ambient lighting conditions. It is especially useful in conjunction with a sphygmomanometer, or blood pressure gauge, with which it will be described herein as an exemplary, but not limiting, embodiment.

Figure 1:
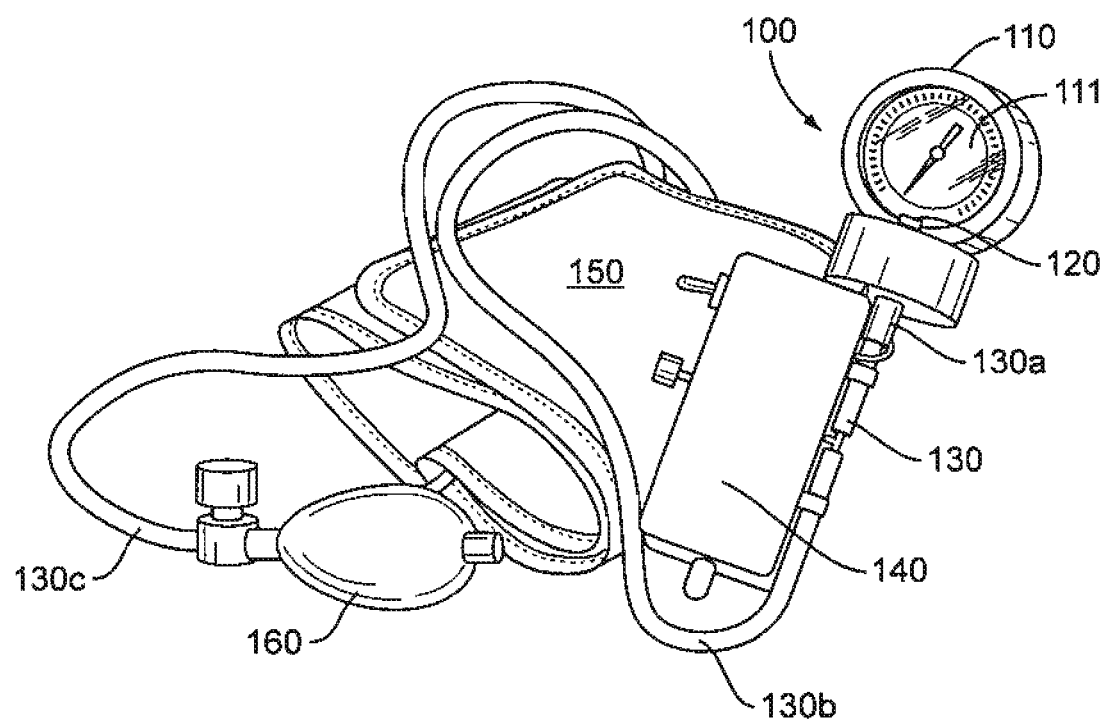
FIG. 1 illustrates a sphygmomanometer including the lighted gauge of the invention.

Referring to FIG. 1, the apparatus 100 includes meter head portion 110 having a dial mechanism 111, a fluid conduit 130, a regulator 140, an arm cuff 150, and a manual pressure source 160.

Figure 2:
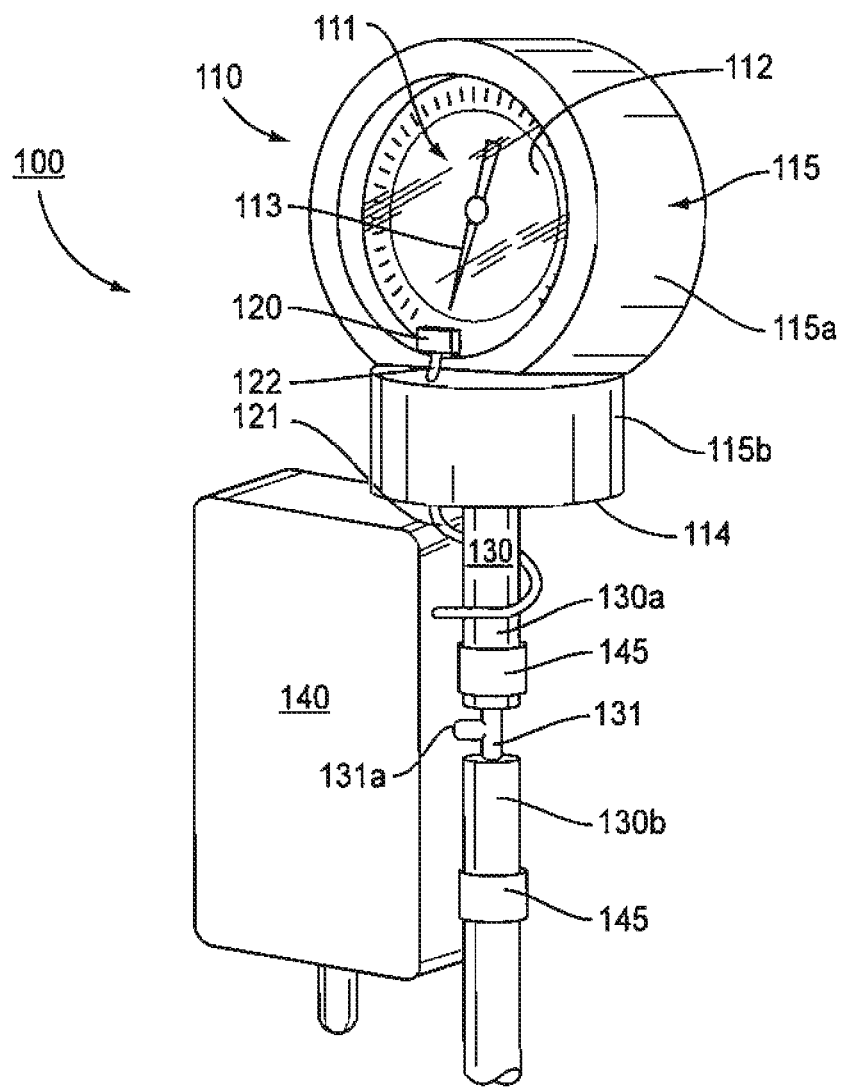
FIG. 2 is a perspective view of the lighted gauge of the invention.

More particularly referring now to FIGS. 1, 2 and 3, meter head 110 includes a cylindrical dial 111 having a transparent face plate 112 of, for example, glass or clear polymeric resin (e.g., acrylic, polycarbonate, etc.), and a base portion 114. An indicator needle 113 is rotatably mounted to the dial to register the blood pressure reading. Meter head 110 preferably includes an elastic fitted sleeve, or cover, 115 having an upper portion 115a at least partially covering the dial 111 and a lower portion 115b at least partially covering the base portion 114.

Referring especially now to FIGS. 2 and 3, a light source 120 is affixed to the elastic fitted sleeve 115 by means of clip 122 in a position separated from, and exterior to, the transparent face plate 112. The light source is oriented to shine light onto the dial face when activated. In a preferred embodiment the light source 120 can be a light emitting diode (LED). Alternatively, light source 120 can be an incandescent light bulb. Electrically conductive wire leads 121 extend between the light source 120 and a power source a provided by a regulator 140.

Referring again to FIG. 1 as well as FIGS. 2 and 3, fluid conduit 130 is connected at one end to the meter head portion 110 and is mounted to regulator 140, optionally by means of brackets 145. An upper first portion 130a of the conduit extends from the meter head 110 to a T-connector 131, which connects upper conduit portion 130a with conduit lower second portion 130b. T-connector 131 includes a branch 131a leading into regulator 140. Conduit second portion 130b extends from the T-connector 131 to the arm cuff 150. Conduit third portion 130c extends from the arm cuff to a pressure source 160. Pressure source 160 comprises a rubber bulb, which can be manually squeezed to send pressure through the conduit 130 into the arm cuff 150 and the meter head 110.

Figure 6:
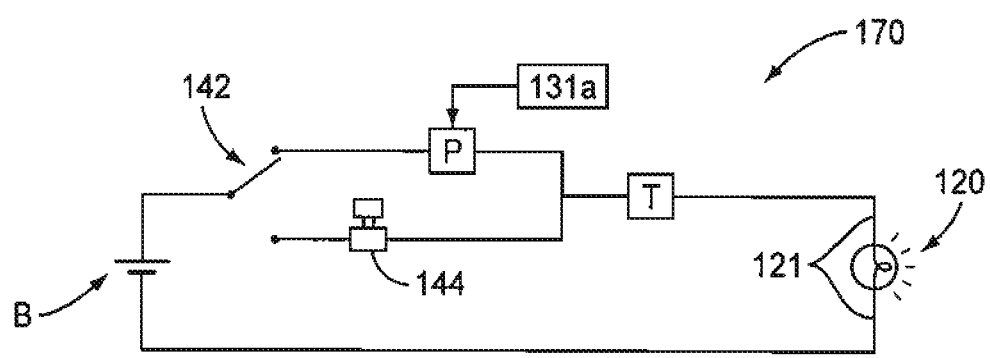
FIG. 6 is a schematic view of an electrical circuit employed in the invention.

Referring now to FIGS. 3, 5 and the schematic circuit diagram 170 of FIG. 6, regulator 140 includes a power source such as battery B within a housing 141. Regulator 140 further includes a toggle switch 142 and a push button switch 144. Toggle switch 142 can be moved between a first position and a second position. In a first position, electrical connection is made to pressure actuated switch P (positioned within housing 141) wherein pneumatic pressure delivered via branch line 131a is communicated to pressure actuated switch P. Apparatus suitable for use as a pressure switch are commercially available and known to those skilled in the art. If the pressure exceeds a predetermined value, pressure switch P closes thereby permitting current to flow therethrough to activate light source 120. Alternatively, if the toggle switch 142 is in a second position, the flow of current is controlled by push button switch 144, not the pressure switch P. When push button switch 144 is pressed, current is allowed to flow therethrough to activate light source 120.

In a preferred but optional embodiment the circuit 170 further includes a timer switch T, which keeps the circuit closed, (i.e., permits current flow therethrough) for a limited predetermined time period. For example, once the light source 120 is activated the timer switch maintains current flow for a period of illumination after which the timer switch T opens and the light source 120 is turned off. By way of example, the period of illumination can range from about 5 seconds to 20 seconds. However, longer or shorter periods of illumination can alternatively be selected.

Referring now to FIGS. 4 and 5, the meter head 110 can also include a clip 150 mounted to the rear surface 117 thereof. Clip 150 includes an upper portion 151 having arms 152, a fulcrum 153 and a lower portion 154. Pressing on the lower portion 154 pivots the upper portion 151 away from the rear surface 117 of the meter head against the biasing force of a spring (not shown) to permit attaching the meter head to a support.

Figure 7:
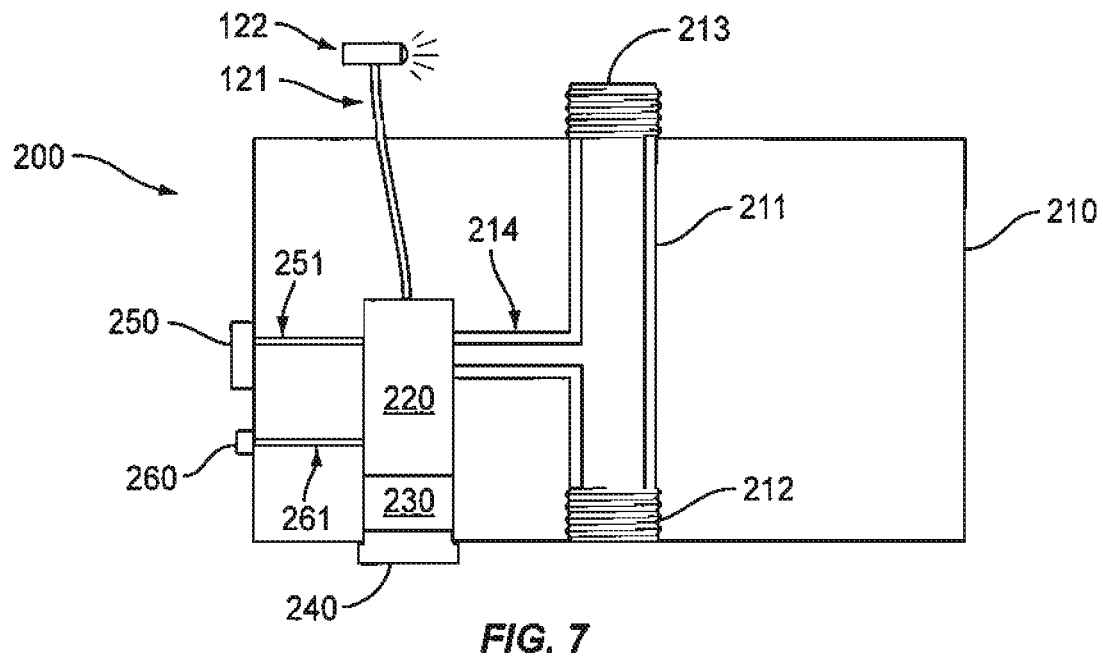
FIG. 7 is a schematic illustration of an adapter for retrofitting the apparatus of the invention onto a gauge; and, FIG. 8 is a front elevational view of the gauge with the retrofitted apparatus mounted thereto.
Figure 8:
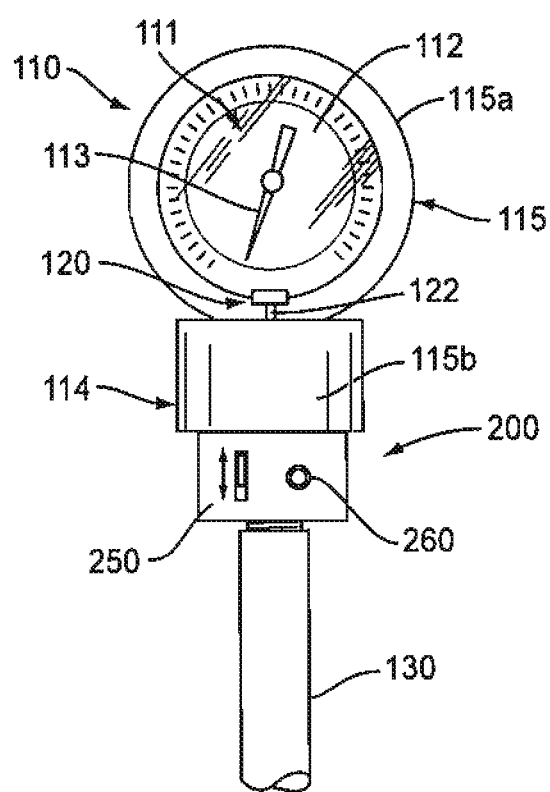

Referring now to FIGS. 7 and 8 an alternative embodiment of the invention is illustrated for retrofit to existing gauges. Embodiment 200 includes an adapter 210 having an internal channel 211 with female and male and threaded ends 212 and 213 adapted to be connected between the conduit 130 and the base 114 of the meter head 110. Channel 211 is a T-connector with branch 214 communicating with regulator 220. Regulator 220 includes an integrated switching circuit to perform the functions of the regulator 140 as described above. Suitable integrated circuit chips for performing the switching function described herein are within the scope of one skilled in the art. Wires 121 communicate with the LED or other such light source 122 mounted to the elastic fitted sleeve 115. Regulator 220 is powered by a battery 230. A removable cap 240 can be used to secure the battery 230 within the adapter 210 and allow for its removal and replacement. Toggle switch 250 is accessible from the outside of the adapter 210 and is connected to the regulator 220 by means of wires 251. The push button switch 260 is likewise accessible from the outside of the adapter 210 and is connected to regulator 220 by means of wires 261.

To retrofit embodiment 200 the conduit 130 is mounted to one end 212 of channel 211 and the adapter is mounted to the meter head 110 at the other end 213 of channel 211. The elastic fitted sleeve 115 is mounted to the meter head 110 and the light source 120 is clipped onto the elastic sleeve 115. The toggle switch 250 is moved to the desired setting.

The invention herein provides significant benefits. The light source 120 illuminates the dial face 111 without obstructing visibility of the indicia on the dial or the position of the indicator needle. Illumination is provided under adverse ambient light conditions and a convenient means for controlling the illumination is provided with options for both automatic illumination upon pressurization, and manual control of illumination by a push-button switch.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A device for illuminating a dial of a gauge comprising:
   a) a dial extending along an axis between an upper portion and a base portion, the upper portion being positioned atop the base portion and comprising a first surface including indicia, the first surface extending parallel to the axis;
   b) a cover configured and dimensioned to fit around the upper portion and the base portion of the dial, the cover comprising a second surface extending perpendicular to the axis that covers the first surface;
   c) a light source mounted to the second surface and positioned to face the first surface so as to illuminate the first surface when said cover is fitted around the dial; and
   d) a regulator electrically connected to the light source, said regulator switching on said light source either (i) automatically in response to actuation of the gauge, or (ii) manually in response to actuation of a regulator first switch associated with said regulator.

2. The device of claim 1 wherein the cover is fabricated from a resilient polymeric material.

3. The device of claim 1, wherein said light source is a light emitting diode.

4. The device of claim 1 wherein the regulator includes a toggle switch movable between a first position wherein the regulator switches on the light source in response to actuation of the gauge, and a second position wherein the regulator switches on the light source in response to manual actuation of the regulator first switch.

5. The device of claim 1 wherein the regulator first switch is a push button switch.

6. The device of claim 1 wherein the regulator includes a power source.

7. The device of claim 1 wherein the regulator comprises an integrated circuit.

8. The device of claim 1 wherein the regulator includes a timer for limiting activation of the light source to a predetermined period of time.

9. The device of claim 1 wherein said device is configured to be retrofitted a sphygmomanometer having a fluid conduit and a dial head.

10. The device of claim 8 wherein the regulator includes a housing enclosing a channel for connection to the fluid conduit of the sphygmomanometer and the dial, said channel being also connected to a pressure switch inside the regulator for activating light source when a predetermined threshold pressure has been reached.

11. An apparatus having a lighted gauge which comprises:
   a) a dial having a front surface with indicia thereon, a transparent face plate covering the front surface and a back surface opposite the front surface; and
   b) a light source positioned exterior to the transparent face plate and oriented to face the front surface so as to illuminate the front surface;
   c) a regulator electrically connected to the light source, and a fluid conduit connected to both the dial and the regulator;
   d) wherein said apparatus is a sphygmomanometer and the fluid conduit is connected to an inflatable arm cuff;
   e) wherein a pressure source is connected to an end of the conduit for pressurizing the inflatable arm cuff;
   f) wherein the regulator includes a toggle switch movable between a first position and a second position, and a push-button switch movable between an on position and an off position, wherein the light source is activated (1) when the toggle switch is in the first position and the arm cuff is pressurized, or (2) when the toggle switch is in the second position and the push button switch is in the on position.

12. The apparatus of claim 11 further including a rubber cover at least partially surrounding the dial wherein the light source is connected to said cover.

13. The apparatus of claim 11 wherein the light source comprises a light emitting diode.

14. The apparatus of claim 11 wherein the light source is activated for a predetermined limited period of time after which it automatically turns off.

15. A method for measuring the blood pressure comprising: a) providing an apparatus including,
   i. a dial having a first surface with indicia thereon and a transparent face plate covering the first surface,
   ii. a light source positioned exterior to the transparent face plate and oriented to face the first surface so as to illuminate the first surface,
   iii. a regulator electrically connected to the light source, and a fluid conduit connected to both the dial and the regulator, wherein the regulator includes a toggle switch movable between a first position and a second position, and a push-button switch movable between an on position and an off position, wherein the light source is activated (1) when the toggle switch is in the first position and the arm cuff is pressurized, or (2) when the toggle switch is in the second position and the push button switch is in the on position,
   iv. an inflatable arm cuff, and
   v. a pressure source connected to an end of the conduit for pressurizing the inflatable arm cuff;
b) wrapping the inflatable arm cuff around an arm of a patient;
c) moving the toggle switch to either the first position or the second position;
d) pressurizing the inflatable arm cuff; and
e) illuminating and viewing the dial.

16. The method of claim 15 wherein the pressure source comprises a rubber bulb and the step of pressurizing the inflatable arm cuff comprises squeezing the rubber bulb multiple times.

* * * * *